United States Patent [19]

Johnson

[11] Patent Number: 4,490,531
[45] Date of Patent: Dec. 25, 1984

[54] PYRIDYL-SUBSTITUTED-BENZOFURANS

[75] Inventor: Roy A. Johnson, Brookline, Mass.

[73] Assignee: The Upjohn Company, Kalamazoo, Mich.

[21] Appl. No.: 430,305

[22] Filed: Sep. 30, 1982

Related U.S. Application Data

[63] Continuation-in-part of Ser. No. 385,622, Jun. 8, 1982, abandoned, which is a continuation-in-part of Ser. No. 279,374, Jul. 1, 1981, abandoned.

[51] Int. Cl.³ ............................................ C07D 405/06
[52] U.S. Cl. .................................... 546/269; 546/270
[58] Field of Search ................................ 546/269, 270

[56] References Cited

U.S. PATENT DOCUMENTS

| | | | |
|---|---|---|---|
| 4,112,224 | 9/1978 | Bundy | 542/426 |
| 4,259,338 | 3/1981 | Paioni et al. | 424/267 |
| 4,271,170 | 6/1981 | Tanouchi et al. | 546/342 |
| 4,410,539 | 10/1983 | Cross et al. | 424/273 R |

FOREIGN PATENT DOCUMENTS

| | | |
|---|---|---|
| 50957 | 5/1982 | European Pat. Off. |
| 2537837 | 3/1976 | Fed. Rep. of Germany |
| 2039903A | 8/1980 | United Kingdom |

OTHER PUBLICATIONS

D. Harris, et al., Advances in Prostaglandin and Thromboxane Research 6:437, (1980).

T. Miyamoto, et al., Advances in Prostaglandin and Thromboxane Research 6:443, (1980).

H. Tai, et al., Advances in Prostaglandin and Thromboxane Research 6:447, (1980).

Primary Examiner—John M. Ford
Assistant Examiner—Bernard I. Dentz
Attorney, Agent, or Firm—Lawrence T. Welch

[57] ABSTRACT

The present invention provides novel pyridinyl-benzofurans and derivatives thereof which are useful as thromboxane $A_2$ ($TXA_2$) synthetase inhibitors and as such represent potent pharmacological agents.

7 Claims, No Drawings

PYRIDYL-SUBSTITUTED-BENZOFURANS

DESCRIPTION

CROSS REFERENCE TO RELATED APPLICATIONS

This application is a continuation in part of copending application Ser. No. 385,622, filed June 8, 1982 now abandoned, which is a continuation in part of Ser. No. 279,374, filed July 1, 1981, now abandoned.

BACKGROUND OF THE INVENTION

The present invention relates to novel compositions of matter. More particularly, the present invention relates to pyridyl substituted benzofurans. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thromboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift No. 2,537,837.

SUMMARY OF THE INVENTION

Thus, the present invention particularly provides: a compound of the formula I wherein $Z_1$ is
(a) 4-pyridinyl,
(b) 3-pyridinyl, or
(c) 3-pyridinyl substituted at the 4 position by
  (1) methyl,
  (2) $-OCH_3$,
  (3) $-N(CH_3)_2$, or
  (4) $NH_2$, or
(d) 3-pyridinyl substituted at the 2, 4, 5, or 6 position by chlorine;
wherein $X_1$ is $-(CH_2)_n-$,
wherein $R_1$ is hydrogen, a pharmacologically acceptable cation, ($C_1$-$C_{12}$) alkyl, ($C_3$-$C_{10}$) cycloalkyl, ($C_7$-$C_{12}$) aralkyl, phenyl, phenyl mono-, di-, or trisubstituted by chloro, ($C_1$-$C_3$) or alkyl, or phenyl para-substituted by
(a) $-NHCO-R_{25}$,
(b) $-O-CO-R_{26}$,
(c) $-CO-R_{24}$,
(d) $-O-CO-(p-Ph)-R_{27}$, or
(e) $-CH=N-NH-CO-NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein $-(p-Ph)$ is 1,4-phenylene;
wherein $R_7$ is
(a) hydrogen,
(b) $-CH_2OH$,
(c) $-COOR_1$,
(d) $-CH_2N(R_4)_2$,
(e) $-CN$
(f) $-CON(R_4)_2$, or
(g) $-C(O)-R_4$;
wherein $R_3$ is
(a) hydrogen,
(b) ($C_1$-$C_3$)alkyl, or
(c) acyl;
wherein $R_4$ is
(a) hydrogen,
(b) ($C_1$-$C_4$)alkyl, or
(c) phenyl;
wherein $R_9$ and $R_{12}$ are the same or different and are
(a) hydrogen,
(b) ($C_1$-$C_4$)alkyl
(c) fluoro,
(d) chloro,
(e) bromo,
(f) $-OCH_3$, or
(g) when taken together and attached to contiguous carbon atoms, $-O-CH_2-O-$;
wherein D represents a single or a double bond;
wherein m is an integer from 0 to 4, inclusive, and wherein n is an integer from 2 to 4, inclusive; including, pharmacologically acceptable acid addition salts thereof; and when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. The salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzofurans, using the Chemical Abstracts numbering system (see Naming and Indexing of Chemical Substances for Chemical Abstracts during the Ninth Collective Period (1972–1976), a reprint of section IV from the Volume 76 Index Guide).

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, two compounds, sodium 6-[2-(3'-pyridinyl)ethyl]benzofuran-2-carboxylate (Example 4) and sodium 5-[2-(3'-pyridinyl)ethyl]benzofuran-2-carboxylate (Example 2), has been shown to be the most effective in inhibiting $TXA_2$ formation. Both compounds have approximate $ED_{50}$'s in this system between 1 and 10 mcg/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g to about 500 $\mu$g/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Charts A–J.

Thus, the compounds of the present invention wherein m is zero are prepared by the method of Chart A. In Chart A, $R_{10}$ is all substituents within the scope of $R_1$ excluding the pharmacologically acceptable cations. All other variables in Chart A are defined as above. A hydroxybenzaldehyde of the Formula X is cyclized into the compounds of the present invention by methods known in the art. See, e.g., S. Tanaka, J. Am. Chem. Soc., 73:872 (1951). Thus, the compound may be reacted with diethyl bromomalonate in the presence of potassium carbonate to yield the desired benzofuran-2-carboxylic acid ester. See, e.g., D. T. Witiak, et al., J. Med. Chem. 21:833 (1978). Higher yields are obtained when the reaction conditions are changed so that the compound is reacted in the presence of sodium hydride in toluene (solubilized with dicyclohexyl-18-crown-6). Conversion of the ester of the Formula XV to the desired pharmacologically acceptable salts or free acid is accomplished by known methods.

The compounds of the Formula X are well known and readily available compounds, and may be prepared from known benzylpyridines of the Formula XX as depicted in Chart B. (See, also, British patent application No. 2,039,903A).

Compounds of the Formula XXIII are prepared according to Chart C. A hydroxybenzaldehyde of the Formula LXXI (wherein P is 0, 1, or 2) is reacted with an appropriate pyridinylalkyltriphenylphosphonium chloride of the Formula LXXII in the presence of n-butyllithium to yield the unsaturated hydroxyphenylalkylpyridine in the Formula LXXIII. Catalytic reduction of the olefinic bonds yields the alkylene bridged compounds of the formula LXXIV.

Related compounds of the Formula XX wherein m is three are disclosed in F. Villani, et al., J. of Pharm. Sciences, 60:1586–1587 (1971). Formula XX compounds wherein m is four are disclosed in B. Baker, et al., J. Med. Chem. 14:793–799 (1971).

Referring to Chart B, a compound of the Formula XX, wherein all variables are defined as above, is nitrated by methods well known in the art, for example, treatment with nitric acid. (While the para nitro compound is the predominant product, the meta and ortho nitro compounds are also formed in smaller quantities. The desired isomer is separated by known methods.) The nitro function is easily reduced by treatment with hydrogen over a 5% palladium-on-carbon catalyst, to form a Formula XXII amine. This amino group is replaced by a hydroxyl moiety via diazotization followed by decomposition of the diazonium salt in hot aqueous acid. Formylation of this phenol to obtain the hydroxybenzaldehyde of the Formula XXIV is accomplished by modification of the Duff reaction (see, J. Duff, J. Chem. Soc. 547 (1941)), by the use of hexamethyltetramine in trifluoroacetic acid, see, W. E. Smith, J. Org. Chem., 37:3972 (1972).

For compounds wherein m is one, the method of Chart D is used. An ester of the Formula XL is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII product. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart E depicts the synthesis of compounds of the present invention wherein m is 2, 3, or 4. In Chart E, q is zero, one, or 2. An ester of the formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formula $Ph_3P=CHCH_2-(CH_2)_qCOOR_{10}$ (wherein Ph is phenyl) yields the unsaturated ester of the Formula LII after workup. Careful reduction of this unsaturated ester by reaction with one equivalent of hydrogen over palladium-on-carbon in alcohol yields the saturated ester of the Formula LIII. The free acid or a pharmacologically acceptable salt of this ester is prepared by means well known in the art. The corresponding amides, phenacyl esters, and the like are prepared by the methods depicted in e.g., U.S. Pat. Nos. 4,292,445 and 4,172,206.

The dihydrobenzofurans are prepared as depicted in Chart F. A solution of a formula LX benzofuran in water is stirred with excess sodium amalgam (NaHg) for 24 hr. After workup there is obtained the corresponding Formula LXI dihydrobenzofuran. (See, e.g., D. T. Witiak, et al., J. Med. Chem. 14, 754 (1971).)

Reduction of the corresponding acid or ester of the formula $COOR_{10}$ with lithium aluminum hydride as depicted in Chart C, (XL to XLI) is used to prepare all of the corresponding alcohols within the scope of Formula I. Conversion of the alcohol to a corresponding acid addition salt is accomplished by known means.

The compounds of this invention wherein m is zero and $R_7$ is hydrogen are prepared by the method of Chart G. A formula LXXV aldehyde is reacted with an appropriate Wittig reagent (prepared by reacting sodium hydride and dimethylsulfoxide with an alkoxyalkyltriphenyl phosphonium halide) to yield the formula LXXVI enol ether. This compound is treated with perchloric acid to yield the formula LXXVII benzofuran.

Chart H depicts a method for preparing chloropyridinyl compounds of this invention. The CV pyridinyl derivative is treated with m-chloroperbenzoic acid to yield the corresponding CVI N-oxide. The N-oxide is treated with phosphorous oxychloride to yield the corresponding chloropyridyl isomers of the formula CVII.

Substituted benzofurans (i.e. compounds wherein $R_9$ and $R_{12}$ are other than hydrogen) are prepared by the methods depicted in Charts I and J.

Chart I depicts a method for preparing brominated derivatives. An aldehyde of the formula CX (prepared by the method of Chart B, see formula XXIV) is treated with bromine to yield the corresponding brominated compound of the formula CXI, which is then converted to the compounds of the present invention by the method of Chart A.

Chart J depicts a method for preparing methyl or methoxy substituted benzofurans or benzothiophenes. In Chart L, $R_{19}$ is methyl or methoxy. The formula CXV ether is hydrolyzed (using hydrobromic acid for example) to yield the formula CXVI alcohol. Similarly, the formula CXV' ether is hydrogenolyzed with hydrogen over palladium on carbon catalyst to yield the formula CXVI alcohol. This alcohol is treated with trifluoroacetic acid in the presence of hexamethylenetetramine to yield the formula CXVII aldehyde, which is converted to the compounds of this invention by the method of Chart A.

Various substituted hydroxy benzaldehydes are available commercially or may be prepared by methods known in the art. The hydroxybenzaldehydes are thus converted to the claimed benzofurans by the method of Chart A.

Compounds where $Z_1$ is 4-methylpyridine are prepared by converting the corresponding 4-chloropyridine of Chart J with methyl magnesium halides to the 4-methyl pyridine derivative according to the procedure described in K. Thomas and D. Jerchel, in "Newer Methods of Organic Chemistry," Vol. III., W. Foerst, ed., Academic Press, N.Y. 1964, pp 74–75.

The 4-methoxy, 4-amino, and 4-N,N-dimethylamino derivatives are prepared from the corresponding 4-methoxy-3-bromopyridine (see T. Talik, Roczniki Chem, 36:1465 (1962)), 3-bromo-4-aminopyridine (see T. Talik, Roczniki Chem., 37:69 (1963)) and 3-bromo-4-dimethylaminopyridine (see J. M. Essery and K. Schofield, J. Chem. Soc., 4953 (1960)), respectively, using the procedure of Chart I (conversion of XCVIII to CI).

Preparation of various other benzofuran derivatives within the scope of this invention are prepared by analogous procedures well known in the art.

Certain compounds of the present invention are preferred. Thus, compounds of the formula I, wherein D denotes a double bond, $Z_1$ is 3-pyridinyl, m is zero, $R_7$ is COOR₁, R₁ is Na or H and R₉ and R₁₂ are hydrogen are preferred. Compounds having all these preferences are more preferred. Thus, sodium 6-[2-(3'-pyridinyl)ethyl]-benzofuran-2-carboxylate and sodium 5-[2-(3'-pyridinyl)ethyl]benzofuran-2-carboxylate are the most preferred compounds of this invention.

DESCRIPTION OF THE PREFERRED EMBODIMENTS

The present invention is seen more fully by the Examples given below.

PREPARATION 1

(E,Z)-1-(4-Hydroxyphenyl)-2-(3-pyridinyl)-ethylene

Refer to Chart C (Conversion of Formulas LXXI and LXXII to Formula LXXIII).

A flask under a dry nitrogen atmosphere is charged with 170 ml of dry tetrahydrofuran and 80 ml (0.128 mol) of 1.6M n-butyllithium in hexane. The flask is cooled in an ice water bath and 3-pyridinylmethyltriphenylphosphonium chloride hydrochloride (17.04 g, 0.04 mol) is added in portions as a solid. A very dark redish-brown slurry results. The ice bath is removed and the mixture is stirred at room temperature for 30 min A solution of 4-hydroxybenzaldehyde (4.0 g, 0.033 mol) in tetrahydrofuran (4.0 g, 0.033 mol) is added dropwise over a 15 min period. The reaction is stirred overnight at room temperature.

The reaction mixture is poured into cold 2N HCl solution in ether (pH ~ 2). The mixture is shaken and then the layers are separated. The aqueous layer is extracted one more time with ether. The aqueous layer is then made basic with saturated NaHCO₃ solution and extracted 4 times with ethyl acetate. The pooled ethyl acetate layers are washed with water, dried over Na₂SO₄, filtered, and evaporated to give a red oil. The oil is chromatographed on 500 g of silica gel. Elution is with 50% ethyl acetate-hexane. 1.50 g of the titled product is obtained as an oil.

The NMR (CDCl₃, δ) peaks observed are 8.53, 8.40,, 7.78, and 7.01.

PREPARATION 2

1-(4-Hydroxyphenyl)-2-(3-pyridinyl)ethane

Refer to Chart C. (Conversion of Formula LXXIII to LXXIV).

The product of Preparation 1 (1.96, 9.9 mol) is reduced by adding the compound to 100 ml of methanol solution and shaking this mixture with 5% Pd on carbon and hydrogen in a Parr apparatus. The catalyst is removed by filtration through sintered glass. 613 mg of the titled product are obtained. The solid is recrystalized from acetone-hexane twice to give 376 mg of crystals with a melting point of 180°–181.5° C.

High resolution mass spectrum reveals the following: Calcd for $C_{13}H_{13}NO$: 199.0997; Found: 199.0996.

IR analysis (nujol) shows peaks observed at 2749, 2684, 2614, 1611, 1593, 1579, 1515, 824, and 803 cm⁻¹.

PREPARATION 3

2-Hydroxy-3-[2-(3'-pyridinyl)ethyl]benzaldehyde

Refer to Chart B. (Conversion of Formula XXIII to XXIV).

Using the method described previously, the phenol of Preparation 3 (757 mg, 3.80 mmol) is reacted with hexamethylenetetramine (546 mg, 3.9 mmol) to form the corresponding aldehyde. A total of 454 mg (53% of theory) of the titled product is obtained after chromatography. This solid is recrystallized from ethyl-pentane to give 370 mg of crystals with a melting point of 63°–64.5° C. The C:H:N ratio is: 73.71:5.92:5.88.

High resolution mass spectrum reveals the following: Calcd. for $C_{14}H_{13}NO_2$: 227.0946; Found: 227.0941.

Other peaks are observed at m/e 199, 135, and 93.

The IR (nujol) spectrum reveals peaks at 2765, 2677, 2603, 2502, 1676, 1612, 1597, 1581, 1502, 1482, 1277, 1246, 908, 826, 801, and 705 cm⁻¹.

The NMR (δ, CDCl₃) peaks observed are 9.82, 8.41, 7.10, and 2.92.

PREPARATION 4

(E,Z)-1-(3-Hydroxyphenyl)-2-(3-pyridinyl)ethylene

Refer to Chart C. (Conversion of Formulas LXXI and LXXII to Formula LXXIII).

A solution of n-butyllithium in hexane (1.6M) (35.5 ml, 60 mmol) is added to 150 ml of benzene in a flask under a dry nitrogen atmosphere. The flask is cooled with an ice-water bath and then 3-pyridinylmethyltriphenylphosphonium chloride hydrochloride (8.52 g 0.020 mol) is added as a solid in several portions. The ice-water bath is removed and the mixture is stirred at room temperature for one hour. 3-Hydroxybenzaldehyde (2.0 g, 0.016 mol) is dissolved in benzene (80 ml, warming is required to achieve solution) and added to the ylid dropwise. The reaction is stirred overnight at room temperature. The reaction is heated at 50° C. for 7.5 hrs. After cooling the contents of the flask are poured into a separatory funnel containing 2N HCl and ice. The pH is made basic (pH approximately 8) with saturated sodium bicarbonate solution. After shaking, the layers are separated. The aqueous layer is then extracted well with ether (4×). All organic layers are combined and washed with water, dried (Na₂SO₄), filtered and evaporated to give 8.5 g of a dark red oil. The oil is chromatographed on 400 g of silica gel packed as a slurry with 25% acetone-hexane followed with 35% acetone hexane. The mixture was eluted in 350 ml fractions. Fractions 31 to 36 yield the minor isomer (0.41 g). The NMR (CDCl₃, δ) showed peaks observed at 8.34 and 8.17.

Fraction 37 yielded a total of 0.59 of mixed products. Fractions 38 to 40 yielded the major isomer (1.27 g).

The NMR (D₂₀-acetone, δ) peaks observed are 8.80 and 8.48.

PREPARATION 5

1-(3-Hydroxyphenyl)-2-(3-pyridinyl)ethane

Refer to Chart C. (Conversion of Formula LXXII to LXXIV).

The major isomer obtained from the Wittig reaction of Preparation 4, (1.27 g, 6.4 mmol) is dissolved in absolute ethanol (50 ml) followed by the addition of 10% palladium/carbon (120 mg). The mixture is hydrogenated at atmospheric pressure for 3 hrs (a total of 175 ml of H₂ is consumed). The reaction mixture is filtered and the solvent is removed at reduced pressure. The crude product is chromatographed on two Merck size B columns with 500 ml of 50% ethyl acetate-hexane followed by 75% ethylacetate-hexane. 0.885 g of the titled product are obtained. The solid is recrystallized from acetone-hexane to give 699 mg of white crystals having a melting point of 107.5°–108.5° C.

The C:H:N ratio is 78.55:6.57:6.66.

High resolution mass spectroscopy reveals the following:

Calcd. for $C_{13}H_{13}NO$: 199.0997; Found: 199.0988

Other peaks are observed at m/e 107, 92, 77, and 65.

The IR spectrum (nujol) reveals peaks at 3060, 2720, 2620, 1620, 1596, 1580, 1525, 1505, 1485, 1285, 1250, 1160, 875, 810, 785, 710, and 700 cm$^{-1}$.

The NMR (CDCl$_3$, $\delta$) spectrum reveals peaks at 8.40, 6.53–7.67, and 2.85.

The minor isomer (0.41 g, 2.1 mmol) is reduced in a similar manner to give, after chromatography, 134 mg of a solid. The solid is recrystallized from acetone-hexane to give white crystals (63 mg) MP 107°–108° C. NMR and IR (mineral oil mull) spectra are identical to those of the product obtained from the reduction of the major isomer.

PREPARATION 6

2-Hydroxy-4-[2-(3'-pyridinyl)ethyl]benzaldehyde

Refer to Chart B. (Conversion of Formula XXIII to XXIV). 1.69 g (8.49 mmol) of the phenol prepared in Preparation 5 in a flask with hexamethylenetetramine (1.26 g, 9 mmol) is dissolved in trifluoroacetic acid (10 ml) and heated in an 80° C. oil. TLC analysis after 45 min reveals that no starting material remains. The reaction is cooled to room temperature and the trifluoroacetic acid is removed under reduced pressure. The residue is stirred for 20 min with 15 ml of water. The mixture is made slightly basic with saturated NaHCO$_3$ and solid NaHCO$_3$ and extracted well with ethyl acetate (5×). The ethyl acetate layers are pooled, washed twice with water, dried (Na$_2$SO$_4$), filtered and evaporated to give 2.00 g of a yellow oil. The oil is chromatographed on 130 g of silica gel packed as a slurry with 50% acetone-hexane. Elution is with 50% acetone-hexane followed by 75% acetone-hexane with 1% triethylamine added. 0.170 g of the titled product are obtained.

The solid is recrystallized twice from ether-pentane to yield 91 mg of white crystals with a melting point of 93°–94° C.

Anal. Calcd. for $C_{14}H_{13}NO_2$: C, 73.99; H, 5.77; N, 6.16; Found: C, 73.57; H, 5.81; N, 5.28; Repeat: C, 73.34; H, 5.84; N, 6.94.

High resolution mass spectroscopy reveals the following:

Calcd. for $C_{14}H_{13}NO_2$: 227.0946; Found: 227.0950.

Other peaks at m/e 199, 135, 107, and 92.

The NMR (CDCl$_3$, $\delta$) peaks observed are 9.85, 8.45, 7.66–6.68, and 2.94.

PREPARATION 7

3-(4'-Nitrobenzyl)pyridine

Refer to Chart B (conversion of Formula XX to XXI).

3-Benzylpyridine (13.52 g, 0.080 mole) and nitric acid (70%, 100 ml) are stirred at 50° C. for 6 hr. The solution is poured into ice-water (1500 ml). The mixture is made alkaline by the careful addition of 50% aqueous sodium hydroxide and then extracted 4 times with 300 ml of ether. The extracts are washed with brine, dried (MgSO$_4$), filtered, and concentrated. The crude product is crystallized from acetone-hexane giving 5.67 g of 3-(4'-nitrobenzyl)pyridine. The filtrate is concentrated and the residue is chromatographed in two equal portions (4.66 g each) over two Merck size C Lobar columns. The columns are eluted with 50% ethyl acetate-hexane. A less polar product [1.83 g, 3-(2'-nitrobenzyl)-pyridine], mixed fractions (1.67 g), and additional 3-(4'-nitrobenzyl)pyridine (2.55 g) after crystallization from acetone-hexane, total 7.92 g, 0.037 mole, 46%). Two recrystallizations from acetone-hexane gives the titled product as colorless needles, having a melting point of 87°–88° C.

The C:H:N ratio is 67.33:4.77:13.23.

From the mixed fractions, 3-(3'-nitrobenzyl)-pyridine is also obtained.

PREPARATION 8

3-(4'-Aminobenzyl)pyridine

Refer to Chart B (conversion of Formula XXI to XXII).

A solution of 3-(4'-nitrobenzyl)pyridine of Preparation 7 (7.924 g, 0.0370 mole) in methanol (100 ml) is shaken with 5% Pd on carbon and hydrogen in a Parr apparatus. Hydrogen uptake is complete within 45 min. The catalyst is removed by filtration through sintered glass. The solvent is removed under reduced pressure. The crystalline residue is recrystallized from methylene chloride-hexane with a first crop of 5.229 g; a second crop of 0.492 g; a third crop of 0.480 g; and a fourth crop of 0.137 g (total 6.338 g, 0.0347 mole, 94%). Recrystallization from CH$_2$Cl$_2$-hexane gives colorless crystals of the titled product with a melting point of 121°–123° C.; IR (nujol) peaks are observed at 3400, 3300, 3200, 1640, 1610, 1590, 1575, 1515, 1480, 845, 800, and 710 cm$^{-1}$.

The C:H:N ratio is 77.91:6.53:15.02.

PREPARATION 9

3-(4'-Hydroxybenzyl)pyridine

Refer to Chart B (conversion of Formula XXII to XXIII).

A solution of sodium nitrite (0.350 g) in water (1.5 ml) is cooled in ice, and added, with stirring, to a cold (ice-bath) solution of 3-(4'-aminobenzyl)pyridine (Preparation 8, 0.920 g, 0.0050 mole) in water (3.75 ml), concentrated sulfuric acid (2.5 ml), and ice (7 g). This solution in turn is added dropwise to a third solution of water (5 ml) and sulfuric acid (6.25 ml) that is maintained at 160° C. in an oil bath. The resulting solution is kept at 160° C. for 10 min and then cooled to room temperature. The pH of the solution is adjusted to 7.0 by addition of aqueous 50% sodium hydroxide. The resulting mixture is extracted 4 times with 25 ml of ether. The aqueous portion is further extracted continuously with ether for 40 hr. The ether extracts are washed with brine, dried over MgSO$_4$, filtered, and concentrated under reduced pressure. The crystalline residue is decolorized with activated charcoal and is recrystallized from acetone-hexane, giving a first crop (0.426 g) of the titled crystals, with a melting point of 182°–185° C. A second crop (0.034 g) and third crop (0.050 g, total 0.510 g, 0.00276 mole, 55%) of titled crystals are also obtained. Recrystallization of the first crop from acetone-hexane gives the titled product as colorless crystals with a melting point of 184°–186° C. IR (nujol) peaks are observed at 2900, 2800, 2720, 2680, 2600, 1615, 1590, 1580, 1515, 1485, 1280, 1250, 845, 800, 710, and 640 cm$^{-1}$.

The C:H:N ratio is 77.97:6.12:7.66.

EXAMPLE 1

Ethyl 5-[2-(3'-pyridinyl)ethyl]benzofuran-2-carboxylate (Formula I, $Z_1$ is 3-pyridinyl, $X_1$ is —$CH_2$—$CH_2$— and is para to the oxygen, $R_9$ and $R_{12}$ are hydrogen, m is zero, the D denotes a double bond, $R_7$ is $COOR_1$, and $R_1$ is ethyl)

Refer to Chart A.

The aldehyde of Preparation 3 (441 mg, 1.94 mmol), methylethylketone (15 ml), diethylbromomalonate (509 mg, 2.13 mmol) and anhydrous potassium carbonate (442 mg, 3.20 mmol) are reacted to obtain 109 mg (19% of Preparation theory) of the titled product as a solid. The solid is recrystallized from ether-pentane to give 43 mg of a white solid 91.5°–92.5° C.

High resolution mass spectroscopy reveals the following:

Calcd. for $C_{18}H_{17}NO_3$: 295.1208; Found: 295.1194.

Other peaks are observed at m/e 250, 203, and 175.

The C:H:N ratio is 72.84:6.22:4.65.

The NMR ($CDCl_3$, δ) peaks observed are 8.38, 7.29, 4.39, and 1.41.

EXAMPLE 2

Sodium 5-[2-(3'-pyridinyl)ethyl]benzofuran-2-carboxylate (Formula I, $Z_1$ is 3-pyridinyl, $X_1$ is —$CH_2$—$CH_2$— and is para to the oxygen, $R_9$ and $R_{12}$ are hydrogen, m is zero, the D denotes a double bond, $R_7$ is $COOR_1$, and $R_1$ is Na)

The ester prepared in Example 1 (92 mg, 0.31 mmol) is hydrolyzed as described in Example 2 to give a white powder. 90 mg of the titled product are obtained.

IR (nujol) peaks observed are at 1620, 1575, 1480, 935, and 790 cm$^{-1}$.

EXAMPLE 3

Ethyl 6-[2(3-pyridinyl)ethyl]-benzofuran-2-carboxylate (Formula I, $Z_1$ is 3-pyridinyl, $X_1$ is —$CH_2$—$CH_2$— and is meta to the oxygen, $R_9$ and $R_{12}$ are hydrogen, m is zero, the D denotes a double bond, $R_7$ is $COOR_1$, and $R_1$ is ethyl)

A solution of the aldehyde of Preparation 6 (155 mg, 0.68 mmol) is treated with anhydrous potassium carbonate (155 mg, 1.13 mmol) and diethyl bromomalonate (130 ml, 179 mg, 0.75 mmol). The mixture is heated at reflux temperature for 23 hrs. The reaction is then cooled to room temperature and poured into water and ethyl acetate. The mixture is shaken and the layers are separated. The aqueous layer is extracted four times with ethyl acetate. The pooled ethyl acetate layers are washed with water, dried over $Na_2SO_4$, filtered and evaporated to give 208 mg of an amber colored oil. The oil is chromatographed on one Merck size A column using 20% acetone-hexane to elute. 60 mg (30% of theory) of the titled product are obtained as a solid.

The product is rechromatographed. 129 mg are obtained as a white solid. A 65 mg portion is recrystallized from ether-pentane to give white crystals (36 mg) with a melting point of 81°–83° C.

The C:H:N ratio is 72.84:6.22:4.65.

High resolution mass spectroscopy reveals the following:

Calcd for $C_{18}H_{17}NO_3$: 295.1208; Found: 295.1203.

Other peaks are observed at m/e 250, 203, 175, and 149. IR (nujol) peaks are observed at 1720, 1678, 1621, 933, 885, 858, 814, 767, and 715 cm$^{-1}$.

NMR ($CDCl_3$, δ) peaks are observed at 8.38, 7.67–6.90, 4.39, 2.98, and 1.39.

EXAMPLE 4

Sodium 6-[2-(3'-pyridinyl)ethyl]benzofuran-2-carboxylate (Formula I, $Z_1$ is 3-pyridinyl, $X_1$ is —$CH_2$—$CH_2$— and is meta to the oxygen, $R_9$ and $R_{12}$ are hydrogen, m is zero, the D denotes a double bond, $R_7$ is $COOR_1$, and $R_1$ is Na)

The ester of Example 3 (124 mg, 0.42 mmol) is dissolved in methanol (4 ml). Sodium hydroxide solution (4.2 ml of 0.1N NaOH) is added with stirring. The reaction is complete after 5 hrs. the methanol is partially removed under reduced pressure. The aqueous residue is frozen in a dry ice-acetone bath and then lyophilized. A white powder is obtained (116 mg).

IR peaks (nujol) are observed at 1610, 1560, 840, 810, 790, and 715 cm$^{-1}$.

TABLE I

FORMULA

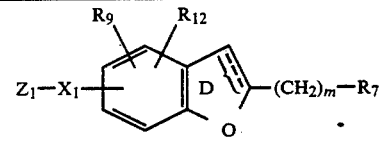

I

CHART A

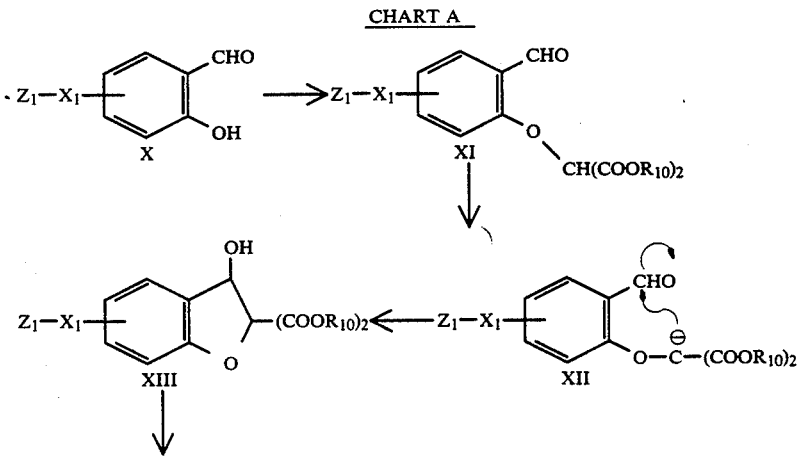

CHART A
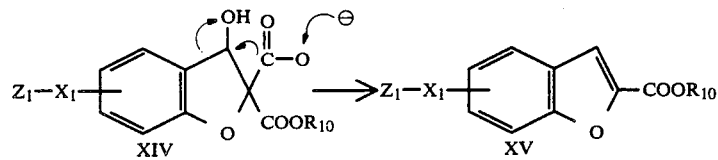
CHART B
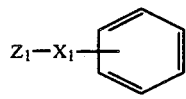
XX
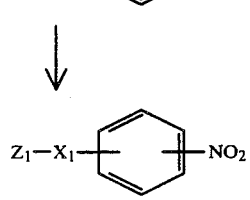
XXI
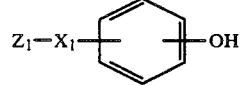
XXII
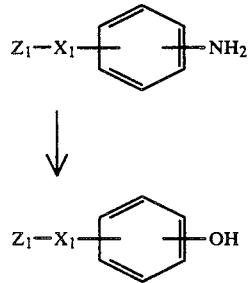
XXIII
-continued
CHART B
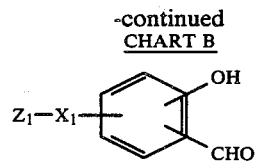
XXIV
CHART C
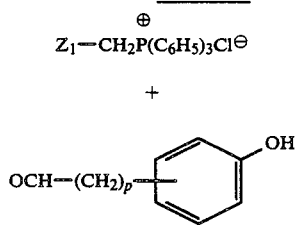
LXXII / LXXI
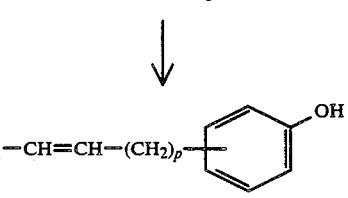
LXXIII
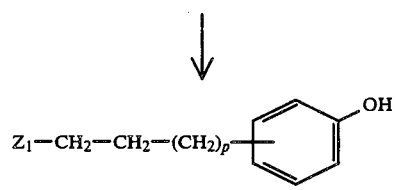
LXXIV
CHART D
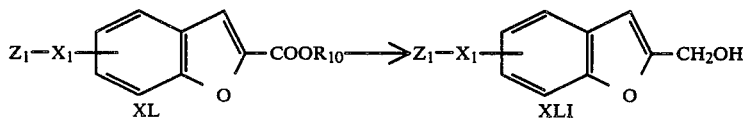
XL → XLI
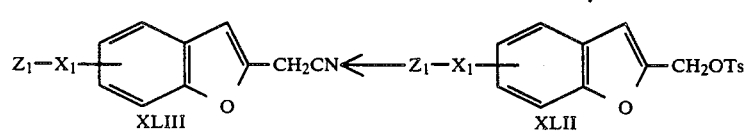
XLIII ← XLII
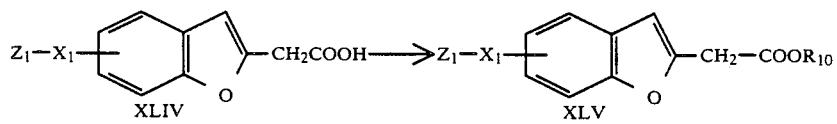
XLIV → XLV

CHART E
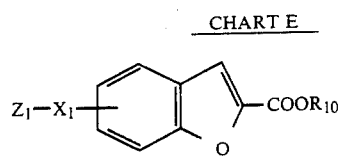
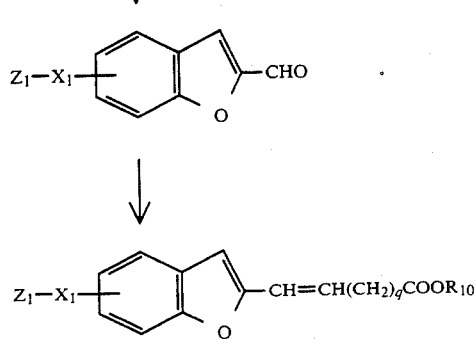
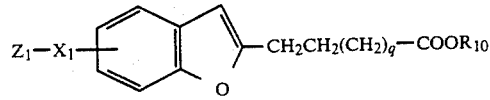
CHART F
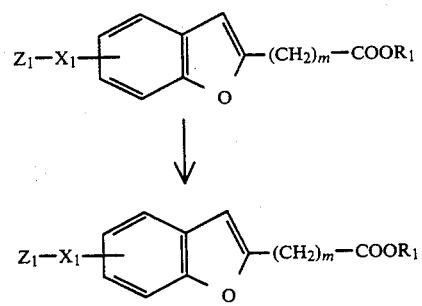
CHART G
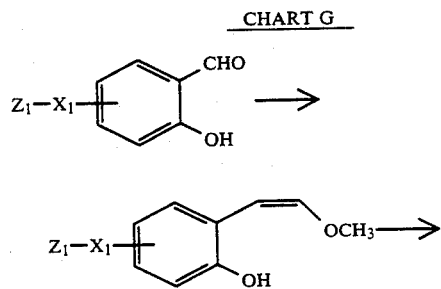
CHART G (continued)
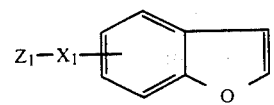
CHART H
CHART I
CHART J
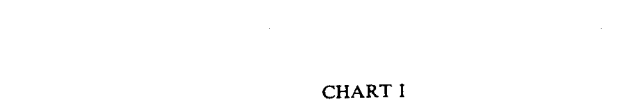
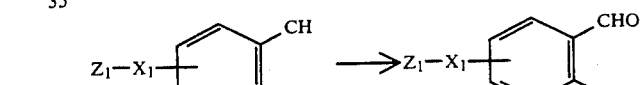
I claim:
1. A compound of the formula I

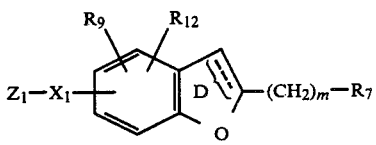

wherein $Z_1$ is
(a) 4-pyridinyl,
(b) 3-pyridinyl, or
(c) 3-pyridinyl substituted at the 4 position by
  (1) —OCH$_3$,
  (2) —N(CH$_3$)$_2$, or
  (3) NH$_2$, or
(d) 3-pyridinyl substituted at the 2, 4, 5, or 6 position by chlorine;
wherein $X_1$ is —(CH$_2$)$_n$—,
wherein $R_1$ is hydrogen, a pharmacologically acceptable cation, (C$_1$–C$_{12}$) alkyl, (C$_3$–C$_{10}$) cycloalkyl, (C$_7$–C$_{12}$) aralkyl, phenyl, phenyl mono-, di-, or trisubstituted by chloro, (C$_1$–C$_3$) alkyl, or phenyl para-substituted by
(a) —NCHO—R$_{25}$,
(b) —O—CO—R$_{26}$,
(c) —CO—R$_{24}$,
(d) —O—CO—(p—Ph)—R$_{27}$, or
(e) —CH=N—NH—CO—NH$_2$,
wherein R$_{24}$ is phenyl or acetamidophenyl, R$_{25}$ is methyl, phenyl, acetamidophenyl, benzamidophenyl, or amino, R$_{26}$ is methyl, phenyl, amino or methoxy; and R$_{27}$ is hydrogen or acetamido, and wherein —(p—Ph) is 1,4-phenylene;
wherein $R_7$ is
(a) —CH$_2$OH,
(b) —COOR$_1$,
(c) —CH$_2$N(R$_4$)$_2$,
(d) —CN, or
(e) —C(O)—R$_4$;
wherein $R_4$ is
(a) hydrogen,
(b) (C$_1$–C$_4$)alkyl, or
(c) phenyl;
wherein R$_9$ and R$_{12}$ are hydrogen;
wherein D represents a single or a double bond;
wherein m is an integer from 0 to 4, inclusive, and wherein n is an integer from 2 to 4, inclusive; including, pharmacologically acceptable acid addition salts thereof;
when D represents a single bond, an enantiomer or a racemic mixture of enantiomers thereof.

2. A compound of claim 1, wherein D denotes a double bond, n is two, m is zero, and R$_7$ is —COOR$_1$.

3. A compound of claim 2, selected from the group consisting of:
ethyl 5-[2-(3'-pyridinyl)ethyl]benzofuran-2-carboxylate,
sodium 5-[2-(3'-pyridinyl)ethyl]benzofuran-2-carboxylate,
ethyl 6-[2(3-pyridinyl)ethyl]-benzofuran-2-carboxylate, and
sodium 6-[2-(3'-pyridinyl)ethyl]benzofuran-2-carboxylate.

4. Ethyl 5-[2-(3'-pyridinyl)ethyl]benzofuran-2-carboxylate a compound of claim 3.

5. Sodium 5-[2-(3'-pyridinyl)ethyl]benzofuran-2-carboxylate, a compound of claim 3.

6. Ethyl 6-[2(3-pyridinyl)ethyl]-benzofuran-2-carboxylate, a compound of claim 3.

7. Sodium 6-[2-(3'-pyridinyl)ethyl]benzofuran-2-carboxylate, a compound of claim 3.

* * * * *